United States Patent

Hsi et al.

[11] Patent Number: 5,415,178
[45] Date of Patent: May 16, 1995

[54] EXTENDABLE GUIDEWIRE ASSEMBLY

[75] Inventors: Bobbie Hsi, Palo Alto; Gene Samson, Milpitas, both of Calif.

[73] Assignee: Target Therapeutics, Fremont, Calif.

[21] Appl. No.: 263,004

[22] Filed: Jun. 17, 1994

Related U.S. Application Data

[63] Continuation of Ser. No. 15,215, Feb. 9, 1993, abandoned, which is a continuation-in-part of Ser. No. 750,558, Aug. 26, 1991, Pat. No. 5,188,621.

[51] Int. Cl.⁶ .............................................. A61B 5/00
[52] U.S. Cl. ................................................. 128/772
[58] Field of Search ................ 128/657, 658, 772; 604/95, 164, 280–283

[56] References Cited

U.S. PATENT DOCUMENTS

| | | | |
|---|---|---|---|
| 4,865,593 | 9/1989 | Ogawa et al. | 604/160 |
| 4,875,489 | 10/1989 | Messner | 128/772 |
| 4,884,579 | 12/1989 | Engelson | 128/772 |
| 4,917,103 | 4/1990 | Gambale | 128/772 |
| 4,922,923 | 5/1990 | Gambale | 128/772 |
| 4,966,163 | 10/1990 | Kraus | 128/772 |
| 5,031,636 | 7/1991 | Gambale | 128/772 |
| 5,109,867 | 5/1992 | Twyford | 128/772 |
| 5,113,872 | 5/1992 | Jahrmarkt et al. | 128/657 |
| 5,117,838 | 6/1992 | Palmer et al. | 128/657 |
| 5,188,621 | 2/1993 | Samson | 604/283 |
| 5,197,486 | 3/1993 | Frassica | 128/772 |

*Primary Examiner*—Max Hindenburg
*Attorney, Agent, or Firm*—Morrison & Foerster

[57] ABSTRACT

An extendable guidewire assembly comprising: a guidewire having a tapered proximal end; an extension wire having a tapered distal end; and a polymeric tubular sleeve reinforced with a helical coil that is fixedly attached about the tapered distal end of the extension wire such that the tapered distal end of the extension wire extends partly through the sleeve lumen, said lumen having a diameter that is smaller than the untapered diameter of the guidewire and wherein said lumen expands radially when the sleeve is under axial compression and contracts radially when the sleeve is under axial tension.

10 Claims, 4 Drawing Sheets

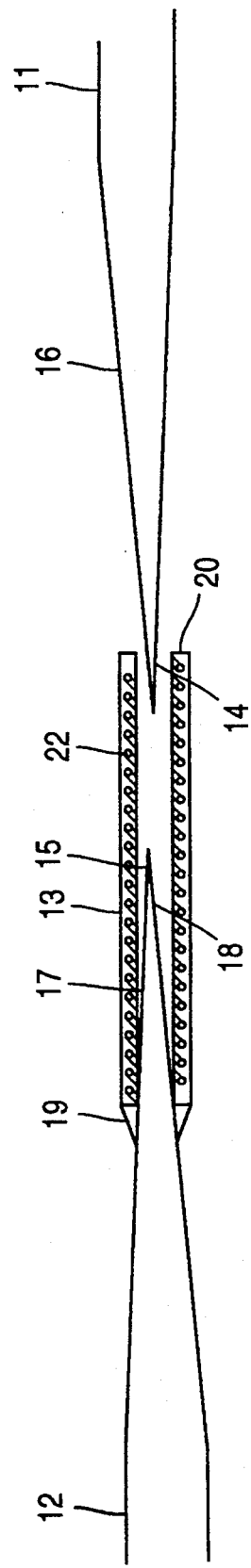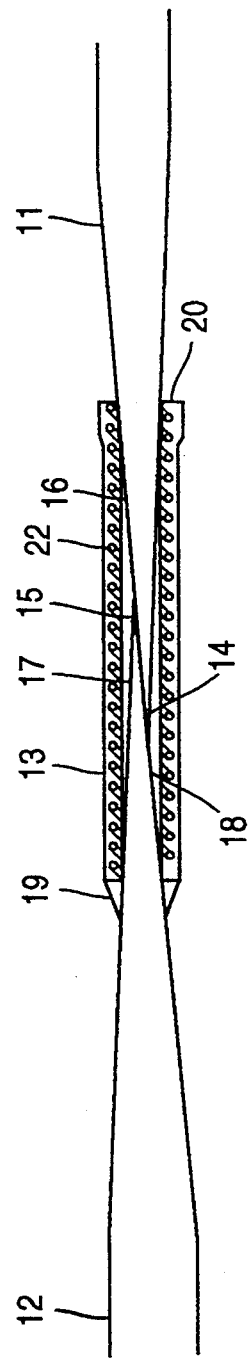

EXTENDABLE GUIDEWIRE ASSEMBLY

This is a continuation of Ser. No. 08/015,215 filed Feb. 9, 1993, now abandoned, which is a continuation-in-part of Ser. No. 07/750,558 filed Aug. 26, 1991, now U.S. Pat. No. 5,188,621.

TECHNICAL FIELD

This invention is in the general field of surgical instruments and relates specifically to an extendable guidewire assembly that is used in cardiovascular and endovascular procedures to facilitate the placement of catheters within the vasculature of patients.

BACKGROUND

The general procedure for placing catheters within vessels is to track a guidewire through the vessel to the desired position and advance the catheter over the guidewire. Guidewires are required because the catheters themselves do not have sufficient column strength or torqueability to be able to be tracked or steered through the vessel. See, for instance, U.S. Pat. No. 4,884,579.

In some procedures such as angioplasty using dilatation balloon catheters, it is necessary to exchange catheters to increase balloon size. It may also be necessary in some instances to replace catheters due to material fatigue. Two guidewire techniques have been employed in such instances. In one, the initial guidewire is removed and replaced with an exchange wire that is somewhat greater than double the length of the catheter. In order to avoid the need for a separate exchange wire a second technique that involves attaching an extension wire to the initial guidewire was developed.

U.S. Pats. Nos. 4,917,103 and 4,922,923 describe an extendable guidewire assembly that employs a sleeve that is connected to the proximal end of the guidewire and into which the distal end of the extension wire is inserted. The sleeve and extension are then crimped to form a permanent joint or union between the two wires.

U.S. Pat. No. 4,875,489 describes another type of extendable guidewire assembly in which one of the wires has a tapered tip and the other has an expandable sleeve into which the tip is received. A second concentric sleeve encloses the expandable sleeve to ensure a friction fit between the tapered tip and expandable sleeve.

U.S. Pat. No. 4,966,163 describes yet another kind of extendable guidewire assembly. In this assembly one of the wires carries an internally threaded sleeve and the other wire carries a threaded head, The two wires are coupled together by threading the head into the sleeve.

U.S. patent application Ser. No. 688,915, filed 19 Apr. 1991, describes an extendable guidewire assembly in which the ends of the guidewire and extension wire carry axial interlocking members and the extension wire carries a retractable sleeve which encloses the interlocked members.

Applicant is also aware of an extendable guidewire assembly design in which one of the wires carries an open-ended sleeve and the other wire has a tapered tip encircled by a helical coil. The wires are coupled by inserting the tip into the sleeve and twisting it. The twisting causes the coil to expand and form a friction fit with the interior of the sleeve. The wires are uncoupled by twisting the tapered tip wire in the reverse direction.

U.S. patent application Ser. No. 07/983,478 filed 1 Dec. 1992 describes an extendable guidewire assembly. A first polymeric sleeve allows for the connection of the guidewire and the extension wire and a second polymeric sleeve acts as a guide to focus the guidewire into the first polymeric sleeve. The application also describes a kit for use in connecting and disconnecting the guidewire assembly. The kit includes the guidewire, the extension wire, the first and second polymeric sleeves and a detachment tool.

A primary object of the present invention is to provide an extendable guidewire assembly with a guidewire and extension wire that can be easily connected and disconnected and that will not kink at the junction of the wires.

DISCLOSURE OF THE INVENTION

The invention is an extendable guidewire assembly for use within a patient's vasculature comprising in combination:

(a) a guidewire having a distal end that is adapted to be fed into said vasculature and a tapered proximal end;

(b) an extension wire having a proximal end and a tapered distal end; and (c) a sleeve comprising a helical coil covered with or embedded in a polymer having first and second ends and a lumen extending therebetween, said first end being fixedly attached concentrically about one of either the proximal end of the guidewire or the distal end of the extension wire such that said one end extends partly through the lumen of the sleeve, said second end being adapted to receive the other of the proximal end of the guidewire or the distal end of the extension wire, said lumen having a diameter that is smaller than the untapered diameter of the wire to which the sleeve is not fixedly attached and wherein the lumen expands radially when the sleeve is under axial compression and contracts radially when the sleeve is under axial tension.

In another embodiment, the invention also includes a second polymeric sleeve having first and second ends and a lumen extending therebetween, said first end having a smaller inside diameter than said second end, said first end being concentric about the first polymeric sleeve, said second end being adapted to receive the proximal end of the guidewire, and to guide the guidewire into the proximal end of the first polymeric sleeve.

BRIEF DESCRIPTION OF THE DRAWINGS

FIG. 1 is a fragmentary elevational view of a preferred embodiment of the extendable guidewire assembly with the guidewire and extension wire in a disconnected configuration.

FIG. 2 is a fragmentary elevational view of the embodiment of FIG. 1 with the guidewire and extension wires in their connected configurations.

Like elements in the drawings bear the same reference numeral.

MODES FOR CARRYING OUT THE INVENTION

Figure 3:
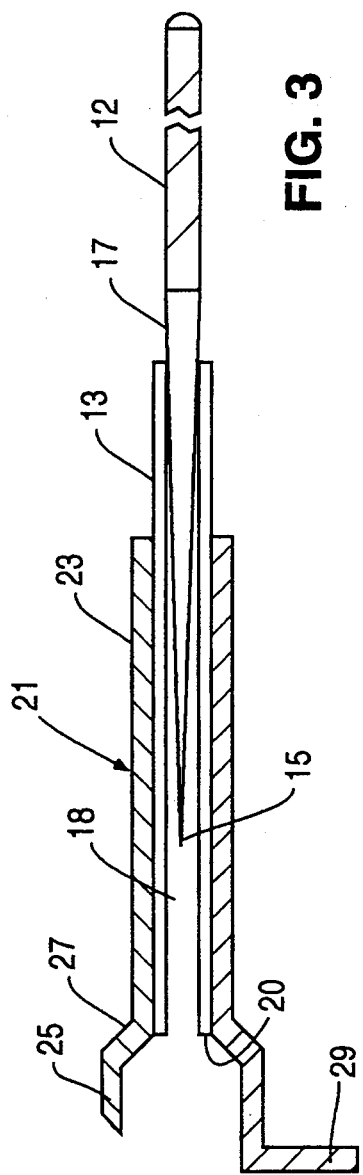
FIG. 3 is a fragmentary elevational view of a second preferred embodiment of the extension wire of the invention with the first and second polymeric sleeves incorporated. The extension wire is shown in a disconnected configuration.

The drawings illustrate the preferred embodiments of the extendable guidewire assemblies of the invention. The three principal components of the first preferred assembly are: a guidewire 11, an extension wire 12, and a sleeve 13. In these figures only the proximal end 14 of the guidewire and the distal end 15 of the extension wire are shown. The remainders of the two wires are not shown and are of conventional structure.

While this invention may be practiced with guidewires of any length and diameter, it will typically be employed with stainless steel or nickel-titanium alloy guidewires and extensions that are $\leq 0.46$ mm in diameter (untapered), more normally 0.25 to 0.40 mm in diameter (untapered). Preferably, the diameters of the guidewire and extension wire are the same. In most instances the length of the guidewire will be in the range of 100–200 cm and the extension will be on the order of 125 to 225 cm in length.

The proximal end 14 of guidewire 11 has a tapered section 16. For manufacturing convenience the taper will normally be conical, although other taper configurations may be used. The taper is continuous and the length of section 16 will normally be 3 to 7 cm, more usually 5 to 6 cm.

The distal end 15 of the extension wire 12 has a similarly tapered section 17. It, too, is preferably conical, continuous and extends over a length of 3 to 7 cm, usually 5 to 6 cm.

Sleeve 13 preferably has an outer diameter that is equal to or less than the outer diameters of the untapered portions of the guidewire and extension wire. Correspondingly, the diameter of its lumen 18 will be less than the individual diameters (untapered) of the two wires. The lumen diameter will typically be 0.2 to 0.36 mm, more usually 0.25 to 0.30 mm. In the embodiment shown in the drawing the sleeve is attached to the tapered end of the extension wire by means of an adhesive 19. Because the diameter of the lumen 18 is smaller than the untapered diameter of the extension wire, the site of affixation is on the tapered portion.

The length of tubular sleeve 13 is such that the tapered portion 17 of the extension wire extends within the lumen over half the length of the sleeve. As shown in the drawing, when the wires are connected the tapered end of the guidewire also extends into the lumen over half the length of the sleeve. Thus, the tapered tips of the wires axially overlap within the lumen. With wires of the dimensions given above, the length of the sleeve will usually be 5 to 8 cm, more usually 6 to 7.5 cm.

The tube is made of a polymer that is reinforced with a helical coil 22 that will provide a friction fit between the contact surface between its inner wall and the tapered section 16 of the guidewire. Further, the nature of the mechanical properties of the polymer and the wall thickness of the sleeve are such that the sleeve will act as a "Chinese finger tube" and its lumen will expand when the sleeve is under axial compression and contract when the sleeve is under axial tension.

The helical coil 22 is preferably formed of a wire or ribbon which can be platinum, stainless steel, or any other biocompatible material stiff enough to support the polymer. The wire or ribbon is coated with or imbedded in the polymer. The polymer may be polyimide or other polymer of like mechanical properties. The wire or ribbon imbedded in the polymer provides a structure which prevents the kinking of the polymeric sleeve 13 during attachment and handling, as well as a serrated outside surface for better gripping for attaching the wires together.

The guidewire and extension wire are connected by simply inserting the tapered end of the guidewire into the sleeve until a tight friction fit between the sleeve and the tapered end of the guidewire is achieved. (See FIG. 2.) Locking of the connection between the wires may be verified by applying axial tension to both wires close to the sleeve junction. Because of the "Chinese finger tube" fit, the wires can be disconnected only by placing force on (gripping) the distal end face 20 of the sleeve, and pulling the tapered end of the guidewire from the lumen. Any manipulation that places the sleeve under axial tension contracts the lumen and exerts radial force at the contact surfaces of the sleeve and the tapered portion of the guidewire.

Figure 4:
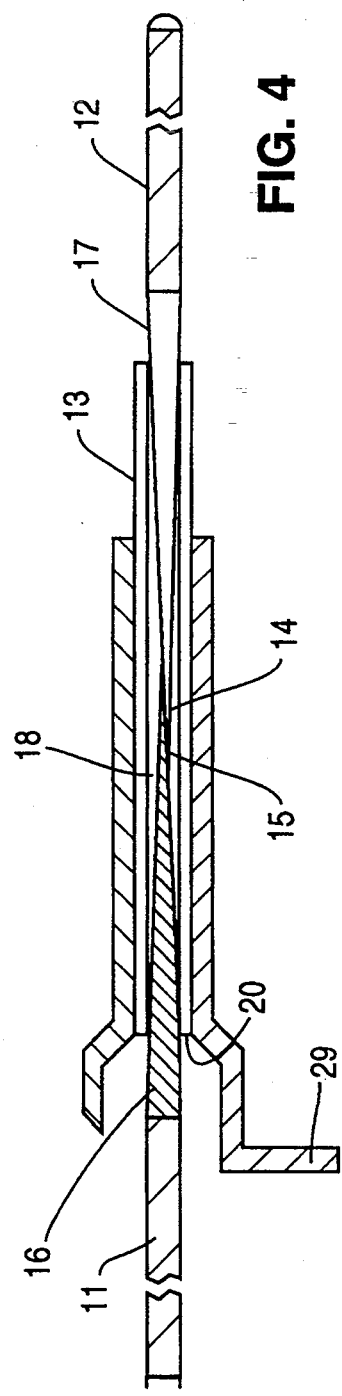
FIG. 4 is a fragmentary elevational view of the embodiment of FIG. 3 with guidewire and extension wires in their connected configuration.
Figure 5:
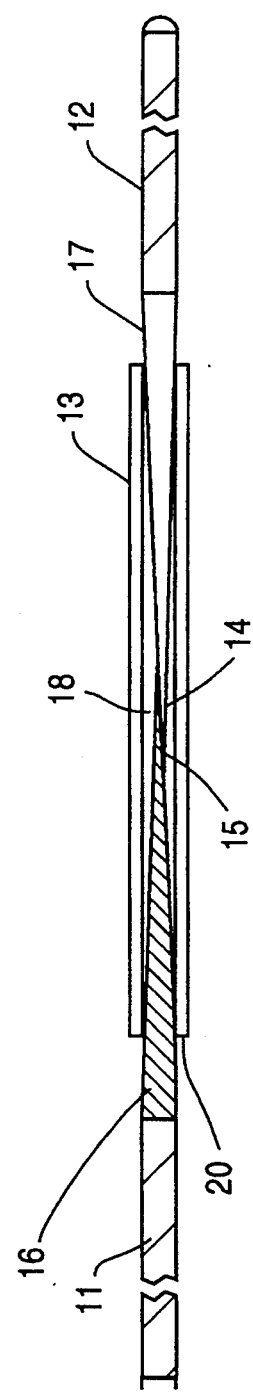
FIG. 5 is a fragmentary elevational view of the embodiment of FIG. 3 with guidewire and extension wires in their connected configuration, with the second polymeric sleeve removed.
Figure 6:
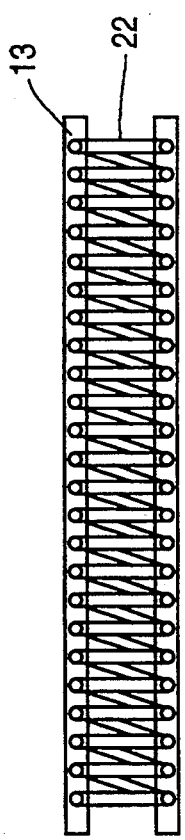
FIG. 6 is a partial side view of the first polymeric sleeve with embedded coil.

In a second embodiment, the extension wire is directed into the first polymeric sleeve 13 by means of a second polymeric sleeve, introducer 21 (See FIGS. 3 and 4). The introducer comprises a polymeric material wherein the proximal end 23 is generally concentric about the first polymeric sleeve 13 described above. The distal end 25 of the introducer 21 has a greater inside diameter than the proximal end 23 such that the guidewire 11 is easily inserted into the introducer (FIG. 4). The introducer contains a tapered section 27 that directs the wire into the first polymeric sleeve 13. When the guidewire 11 is securely in place inside the first polymeric sleeve 13, the introducer is removed (FIG. 5). In the embodiment shown in FIGS. 3 and 4 the introducer has a slit along the entire length of its proximal 23 and distal 25 segments. Following insertion of the proximal end 14 of guidewire 11, the introducer 21 is peeled away by grasping tab 29 and pulling. The slit in the introducer is thereby opened and the introducer can easily be pulled off of the extension wire and guidewire assembly.

The proximal end 23 of introducer 21 preferably has an inner diameter that is smaller than the outer diameter of sleeve 13. The inner diameter of proximal end 23 will typically be 0.22 to 0.46 mm, more usually 0.28 to 0.30 mm. The distal end 25 of the introducer 21 preferably has an inner diameter that is large enough for easy insertion of the guidewire 11. The inner diameter will typically be 0.5 to 3.0 mm, more usually 0.6 to 1.4 mm. The length of the introducer is such that the sleeve 13 extends within the lumen of the introducer 21 over half the length of the first polymeric sleeve 13. As shown in the drawings, when the wires are connected, the tapered end of the guidewire also extends into the lumen over half the length of the introducer. With wires of the dimensions given above, the length of the introducer will usually be 3 to 10 cm, more usually 3.5 to 5 cm.

The introducer 21 is made of polymeric tubing. The material is such that it has the mechanical strength to withstand the insertion of the guidewire, but can be easily peeled away when the insertion is complete. In this regard, the wall thickness of the introducer will usually be 0.10 to 0.13 mm and the introducer will be made of 1 to 5 mm outer diameter polyethylene tubing. The introducer may also be made of tubing of other polymers of like mechanical properties.

An extendable guidewire assembly according to the invention was made as follows. Using a centerless grinder, the proximal end of a 195 cm long stainless steel catheter guidewire having a 0.014" OD was ground to 0.002" tip OD with a 6.0 cm taper length. The end of a different wire of the same diameter, about 160 cm long, was ground similarly as the guidewire. This wire served as the extension wire. Polyimide tubing reinforced with a helical coil comprising a metal ribbon (purchased from Hudson International) with a 0.013" OD and a 0.001" wall thickness was cut squarely to about 7.5 cm long. The ends of the tubing were carefully sanded to remove any remaining burrs from the imbedded ribbon. A thin film of epoxy adhesive was applied on the ground segment of the extension wire. The tip of the extension wire was inserted into the polyimide tubing and pressed until the wire locked. The epoxy was allowed to cure overnight. Alternatively the epoxy may be cured by heating for 3 min at $\approx 135°$ C. Extension of the guidewire was accomplished by inserting the ground proximal end of the guidewire into the polyimide spiral reinforced tube of the extension wire. The catheter wire was pressed firmly into the tubing.

Where the extension wire and guidewire assembly included an introducer, the introducer was formed from polyethylene tubing according to the following procedure.

A 7.5 cm length of tubing with an outer diameter of 2 mm was cut. Heat was applied to the proximal end 23 of the tubing in order to form a section that is 4 cm long and has an inner diameter of about 0.30 mm. The tab 29 was similarly formed by heat shrinking the section of tubing that comprises the tab until the tubing had an outer diameter of about 0.89 mm and was about 1 cm long.

In order that the introducer be removable after the guidewire has been inserted, a slit was cut the length of the introducer. The introducer was slid into place over the first polymeric sleeve 13 and shrunk fit over the first polymeric sleeve to secure it in place. An opening dimensioned 2 by 4 mm was cut in the distal end 25 of the introducer 21 such that the proximal end 14 of guidewire 11 could easily be inserted into the introducer.

Figure 7:
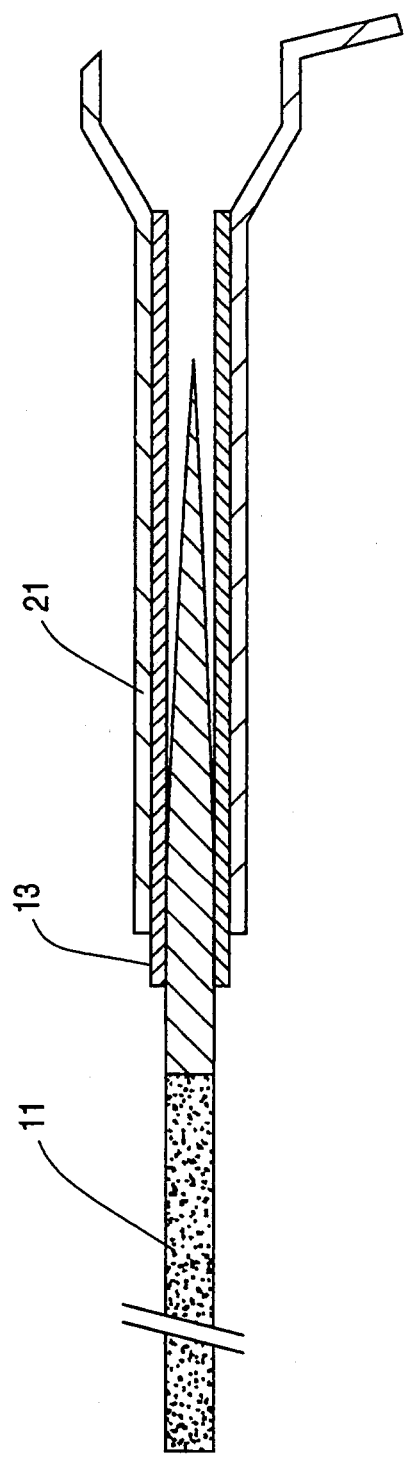
FIG. 7 is a fragmentary elevational view of the guidewire of the invention with the first and second polymeric sleeves incorporated.

While the above-described embodiments show the first and second polymeric sleeves affixed to the extension wire, it will be appreciated that the respective wire structures may be reversed as shown in FIG. 7 (i.e., the sleeves 13 and 21 are affixed to the proximal end of the guidewire 11). Similarly, other modifications of the above-described embodiment of the invention that are obvious to those of skill in the mechanical and guidewire/catheter arts are intended to be within the scope of the following claims.

We claim:

1. An extendable guidewire assembly for use within a patient's vasculature comprising in combination:

(a) a guidewire having a distal end that is adapted to be fed into said vasculature and a tapered proximal end;
    (b) an extension wire having a proximal end and a tapered distal end; and
    (c) a first polymeric sleeve comprising a helical coil covered with or embedded in a polymer having first and second sleeve ends and a lumen extending therebetween along an axis, said first sleeve end attachable concentrically about one of either the proximal end of the guidewire or the distal end of the extension wire, such that said proximal end of the guidewire or the distal end of the extension wire is extendible partly through the lumen of the first polymeric sleeve, said second sleeve end being attachable concentrically to the other of the proximal end of the guidewire or the distal end of the extension wire, said lumen having a diameter that expands radially when the sleeve is under axial compression during introduction of the proximal end of the guidewire or the distal end of the extension wire and contracts radially when the sleeve is under axial tension.

2. The guidewire of claim 1 additionally comprising a second polymeric sleeve having first and second ends and a lumen extending therebetween, said first end having a smaller inside diameter than said second end, said first end being concentric about the first polymeric sleeve, said second end being adapted to receive the proximal end of the guidewire, and to guide the guidewire into the proximal end of the first polymeric sleeve.

3. The extendable guidewire assembly of claim 1 wherein the first polymeric sleeve is fixedly attached about the distal end of the extension wire.

4. The extendable guidewire assembly of claim 1 wherein the taper of the proximal end of the guidewire is a conical taper and the taper of the distal end of the extension wire is a conical taper.

5. The extendable guidewire assembly of claim 1 wherein said one end to which the sleeve is fixedly attached extends through greater than half the length of the sleeve lumen.

6. The extendable guidewire assembly of claim 1 wherein the untapered diameter of the guidewire is about 0.3 to 0.4 mm, the untapered diameter of the extension wire is about 0.3 to 0.4 mm, and the diameter of the sleeve lumen is less than said untapered diameter of the guidewire.

7. The extendable guidewire assembly of claim 6 wherein the length of the tapered end of the guidewire is 3 to 7 cm, the length of the tapered end of the extension wire is 3 to 7 cm.

8. The extendable guidewire assembly of claim 7 wherein the sleeve has a wall thickness of 0.025 to 0.05 mm.

9. The extendable guidewire assembly of claim 1 wherein the polymer is polyimide and the helical coil is formed of metal ribbon.

10. The extendable guidewire assembly of claim 1 wherein the polymer is polyimide and the helical coil is formed of metal wire.

* * * * *